United States Patent
Lyster

(10) Patent No.: US 9,744,370 B2
(45) Date of Patent: *Aug. 29, 2017

(54) AED HAVING CPR PERIOD WITH PAUSE FOR ECG ACQUISITION

(71) Applicant: KONINKLIJKE PHILIPS N.V., Eindhoven (NL)

(72) Inventor: Thomas Lyster, Lopez Island, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 15/279,819

(22) Filed: Sep. 29, 2016

(65) Prior Publication Data

US 2017/0014636 A1    Jan. 19, 2017

Related U.S. Application Data

(63) Continuation of application No. 12/517,223, filed as application No. PCT/IB2007/054878 on Nov. 30, 2007, now Pat. No. 9,474,907.

(60) Provisional application No. 60/869,014, filed on Dec. 7, 2006.

(51) Int. Cl.
   *A61N 1/00*    (2006.01)
   *A61N 1/39*    (2006.01)

(52) U.S. Cl.
   CPC ............. *A61N 1/3925* (2013.01); *A61N 1/39* (2013.01); *A61N 1/3987* (2013.01)

(58) Field of Classification Search
   CPC ....... A61N 1/39; A61N 1/3925; A61N 1/3987
   See application file for complete search history.

(56) References Cited

U.S. PATENT DOCUMENTS

| | | | |
|---|---|---|---|
| 6,306,107 B1 | 10/2001 | Myklebust et al. | |
| 6,314,320 B1 | 11/2001 | Powers et al. | |
| 6,356,785 B1 | 3/2002 | Snyder et al. | |
| 6,553,257 B2 | 4/2003 | Snyder et al. | |
| 7,039,457 B2 | 5/2006 | Young et al. | |
| 9,474,907 B2* | 10/2016 | Lyster | A61N 1/39 |
| 2002/0133197 A1 | 9/2002 | Snyder et al. | |
| 2004/0162585 A1 | 8/2004 | Elghazzawi et al. | |
| 2004/0176807 A1* | 9/2004 | Freeman | A61H 31/005 607/5 |
| 2005/0267536 A1 | 12/2005 | Freeman et al. | |

(Continued)

FOREIGN PATENT DOCUMENTS

| WO | 0156652 A | 8/2001 |
|---|---|---|
| WO | 2006105398 A | 10/2006 |

(Continued)

*Primary Examiner* — Lindsey G Wehrheim

(57) ABSTRACT

A method for using a defibrillator is described which executes a resuscitation protocol having a CPR pause period. The defibrillator prompts a rescuer to perform CPR during a CPR pause period. The CPR pause period may be interrupted for the acquisition of ECG signal data which is not contaminated by chest compression artifacts. Following the acquisition of ECG signal data, the CPR period resumes and continues for its full period. The ECG signal data acquired during the interruption of the CPR period is analyzed and, if a shockable rhythm is identified, a shock sequence is initiated immediately upon conclusion of the CPR period.

13 Claims, 5 Drawing Sheets

(56) References Cited

U.S. PATENT DOCUMENTS

| | | |
|---|---|---|
| 2006/0116724 A1 | 6/2006 | Snyder |
| 2006/0122648 A1 | 6/2006 | Elghazzawi et al. |
| 2006/0149157 A1 | 7/2006 | Weil et al. |
| 2006/0229680 A1 | 10/2006 | Chapman et al. |

FOREIGN PATENT DOCUMENTS

| | | |
|---|---|---|
| WO | 2006136974 A2 | 12/2006 |
| WO | 2007069162 A1 | 6/2007 |

\* cited by examiner

AED HAVING CPR PERIOD WITH PAUSE FOR ECG ACQUISITION

This is a continuation of U.S. Ser. No. 12/517,223, filed Jun. 2, 2009, which is a U.S. National Phase Application of International Application No. PCT/IB2007/054878, filed on Nov. 30, 2007 and claims the benefit of U.S. Provisional No. 60/869,014, filed on Dec. 7, 2006.

The invention generally relates to medical equipment, and more particularly, to automatic external defibrillators providing combined defibrillation and CPR pause modes of operation.

Defibrillators deliver a high-amplitude current impulse to the heart in order to restore normal cardiac rhythm and contractile function in patients who are experiencing arrhythmia, such as ventricular fibrillation ("VF") or ventricular tachycardia ("VT") that is not accompanied by a palpable pulse. There are many classes of defibrillators, including manual defibrillators and automatic external defibrillators ("AEDs"). AEDs differ from manual defibrillators in that AEDs can automatically analyze patient electrocardiogram ("ECG") rhythm to determine if defibrillation is necessary. In most AED designs, the user is prompted to press a shock button to deliver the defibrillation shock to the patient.

AEDs are typically configured to provide a user with visual or audio prompts to carry out a medical protocol that includes both delivery of electrotherapy as well as performing cardio-pulmonary resuscitation ("CPR"). Research has shown that the application of early and extensive CPR can increase the chances of survival, particularly for patients who have been in VF for many minutes prior to treatment. Accordingly, resuscitation protocols have been developed to both detect and treat VF as well as guide the rescuer in the administration of CPR. For example, PCT patent application number IB2006/051897 (Snyder et al.) describes an AED with a protocol that selects either a shock-first or a CPR-first protocol based upon ROSC scoring. U.S. Pat. No. 6,553,257 (Snyder et al.) and US patent application publication no. 2006/0116724 (Snyder) describe an AED which is prepared for shock delivery prior to the end of the CPR pause period so that a shock can be delivered promptly following CPR if advised. Several patents such as U.S. Pat. No. 7,039,457 (Young et al.) and US patent application publication no. 2006/0149157 (Weil et al.) propose to acquire and analyze the patient's ECG while CPR is being administered, and to discern the heart waveform from the artifacts created by the CPR compressions by the irregularity and high amplitude of the artifacts. This is said to be an improvement over prior art approaches in which CPR is interrupted for a "quiet" period of 12 to 25 seconds while the defibrillator acquires and analyzes the ECG waveform without interruption from artifacts, then delivers a shock if advised. However the accurate detection of a VF ECG waveform nevertheless presents a serious challenge for most artifact removal techniques. Consequently the acquired ECG data should be checked for artifacts before it is accepted for analysis. Discovery of artifact contamination can result in rejection of all of the data of the analysis window, requiring another attempt at ECG acquisition which further delays treatment. Accordingly it is desirable to maximize the time during CPR pause periods for the delivery of chest compressions and ventilation while at the same time promptly reliably delivering a shock if advised.

In accordance with the principles of the present invention, a defibrillator monitors for breaks in CPR administration, preferably by sensing CPR activity from small signal chest impedance measurement. If a break is detected, ECG signal data is acquired and analyzed. If no break in CPR occurs, a pause in CPR administration is prompted and ECG signal data is acquired and analyzed during the prompted break. The CPR period is resumed and completed, at which time a shock is delivered if advised. In accordance with a further aspect of the present invention, the ECG analysis is used in a V-rhythm assessment of the success of resuscitation and, if success is indicated and a shock is advised, the CPR period is terminated immediately for shock delivery.

Figure 1:
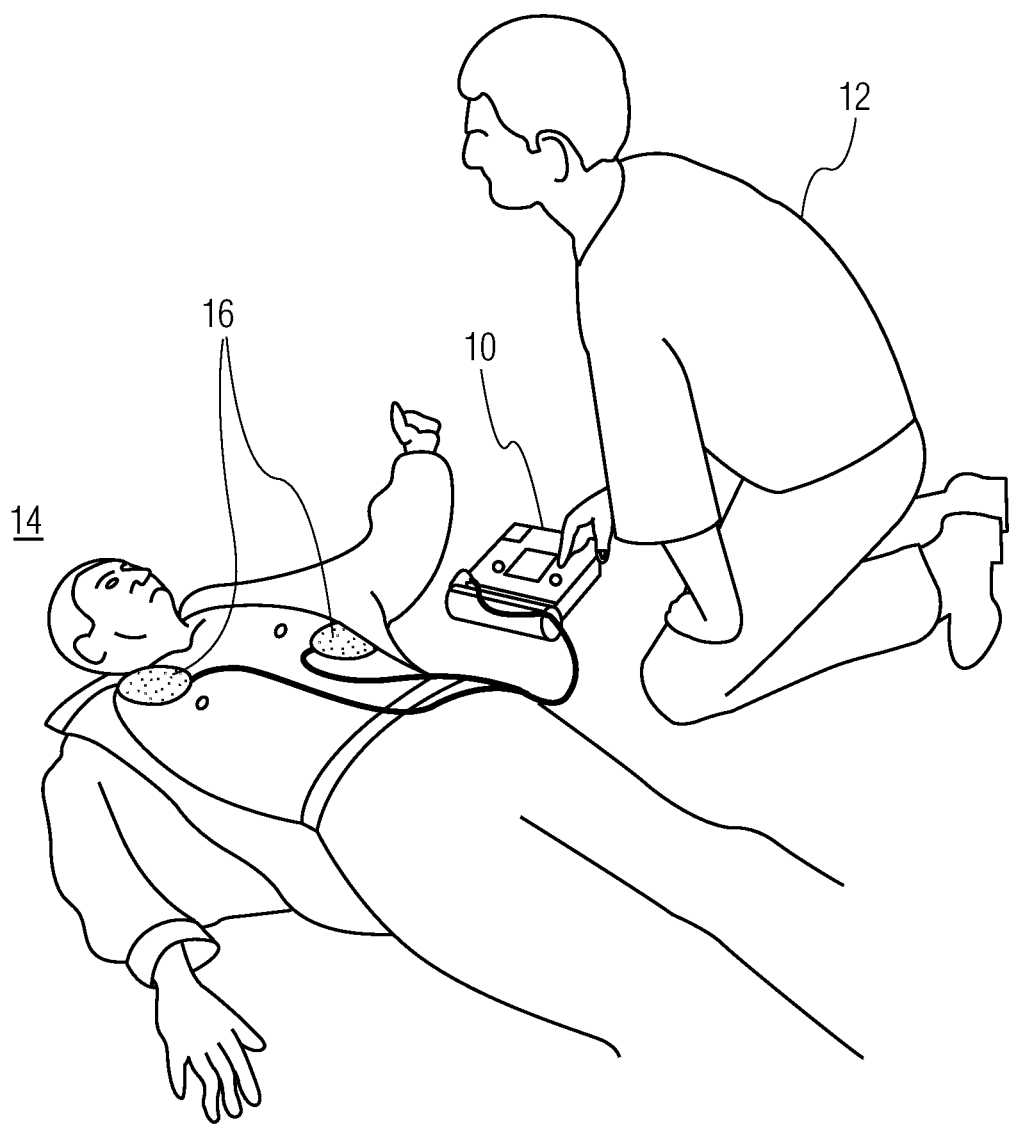
FIG. 1 is an illustration of a defibrillator being applied to a patient suffering from cardiac arrest.

Referring first to FIG. 1, an AED 10 is illustrated being applied by a user 12 to resuscitate a patient 14 suffering from cardiac arrest. In cardiac arrest, the patient is stricken with a life threatening interruption to the normal heart rhythm, typically in the form of VF or VT that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be applied after the onset of VF, the better the chances that the patient 14 will survive the event.

A pair of electrodes 16 are applied across the chest of the patient 14 by the user 12 in order to acquire an ECG signal from the patient's heart. The AED 10 then analyzes the ECG signal for signs of arrhythmia. If VF is detected, the AED 10 signals the user 12 that a shock is advised. After VF or other shockable rhythm has been identified by the AED, the user 12 presses a shock button on the AED 10 to deliver a defibrillation pulse to resuscitate the patient 14.

Figure 2:
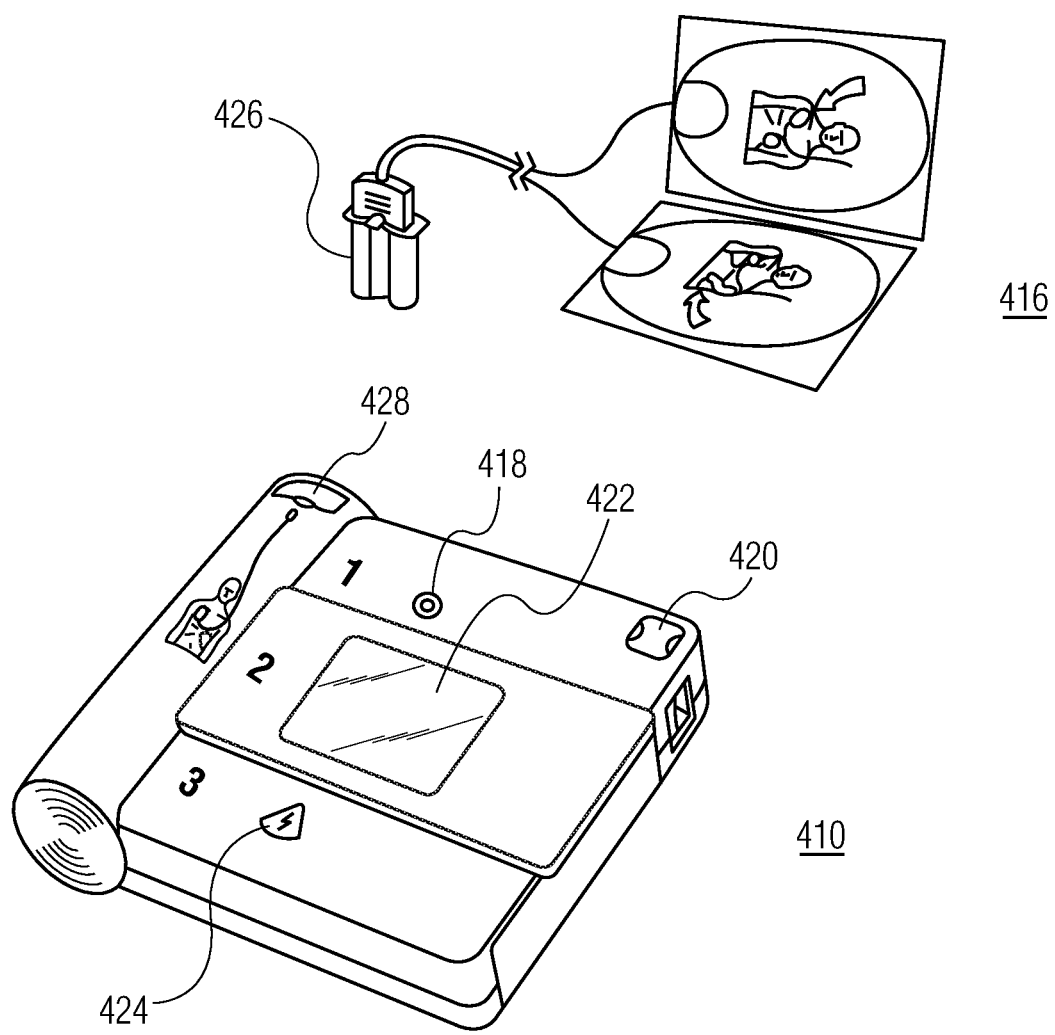
FIG. 2 is an illustration of a defibrillator and electrodes in which a combined monitor and CPR pause mode of operation according to an embodiment of the present invention can be implemented.

FIG. 2 illustrates a defibrillator according to an embodiment of the present invention. For purposes of the discussion that follows, the defibrillator is configured as an AED 410, and is designed for small physical size, light weight, and relatively simple user interface capable of being operated by personnel without high training levels or who otherwise would use the AED 410 only infrequently. A clinical or hospital defibrillator used by medical professionals, on the other hand, tends to be larger, heavier, and have a more complex user interface capable of supporting a larger number of manual monitoring and analysis functions. Although the present embodiment of the invention is described with respect to application in an AED, other embodiments include application in different types of defibrillators, for example, manual defibrillators, and paramedic or clinical defibrillators.

A pair of electrodes 416 is connected to a connector 426 for insertion into a socket 428 of the AED 410. Located on a top surface of the AED 410 is an on-off switch 418 that activates the AED 410 and begins the process of the prompting the user to apply the electrodes 416 to the patient. A status indicator 420 provides a continual visual indication of the defibrillator status and the available battery charge. A display 422 preferably provides for display of text such as user prompts and graphics such as ECG waveforms. A shock button 424 provides for delivery of the shock to the patient if ECG analysis indicates that a shockable rhythm is present. Administration of defibrillation shocks is done by prompting the user to manually press the shock button 424.

Figure 3:
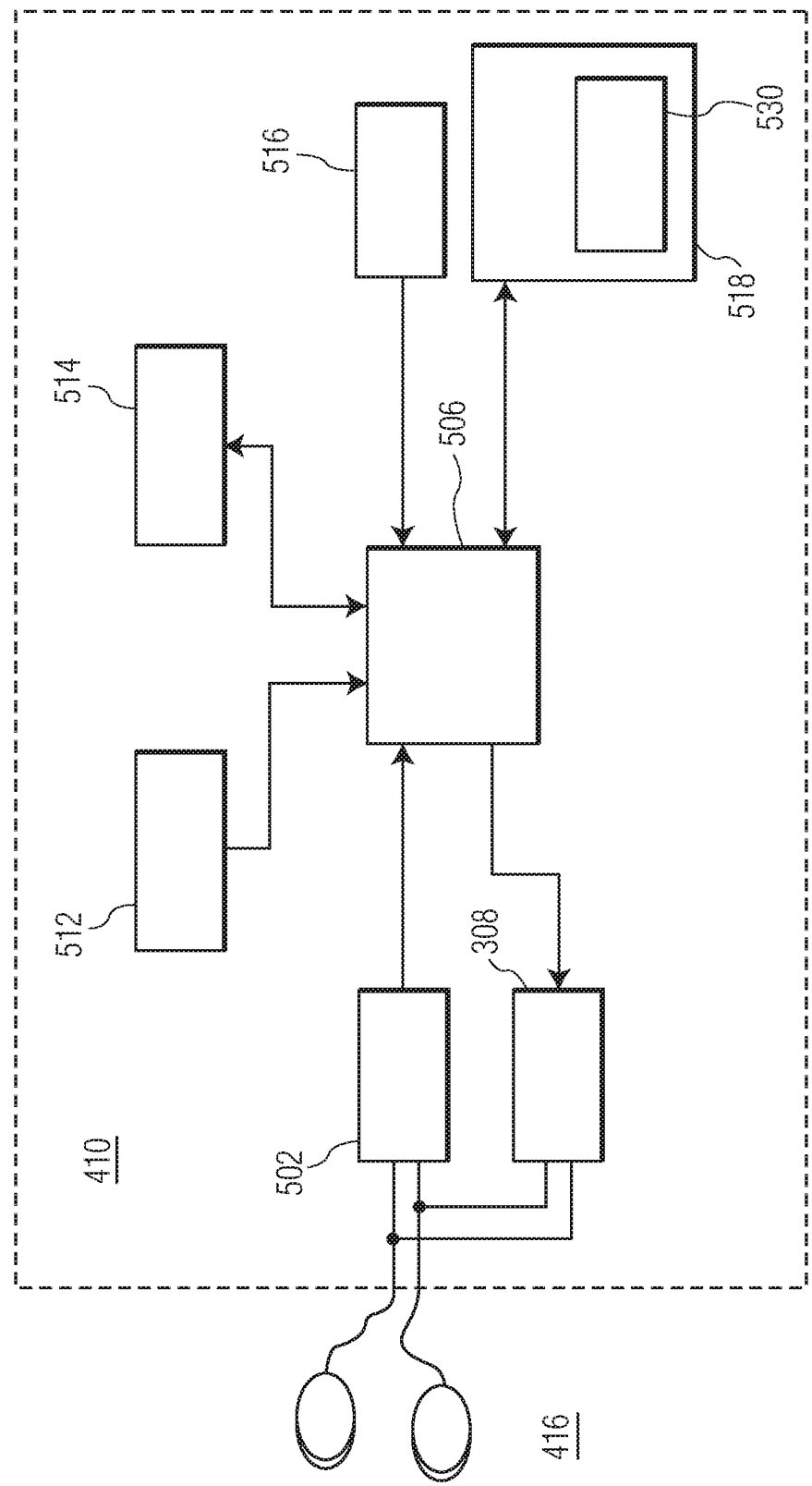
FIG. 3 is a is a simplified block diagram of the defibrillator of FIG. 2.

FIG. 3 is a simplified block diagram of the AED 410 according to an embodiment of the present invention. An ECG front end 502 is connected to the pair of electrodes 416 that are connected across the chest of the patient 14. The ECG front end 502 operates to amplify, buffer, filter and digitize an electrical ECG signal generated by the patient's heart to produce a stream of digitized ECG samples. The digitized ECG samples are provided to a controller 506 that performs an analysis to detect VF, shockable VT or other shockable rhythm. If a shockable rhythm is detected, the controller 506 sends a signal to HV delivery circuit 508 to charge-up in preparation for delivering a shock. Pressing the shock button 424 then delivers a defibrillation shock from the HV delivery circuit 508 to the patient through the electrodes 416. As will be described in more detail below, the controller can be configured to implement a combined defibrillation and CPR pause mode of operation.

The controller 506 is coupled to further receive input from a microphone 512 to produce a voice strip. The analog audio signal from the microphone 512 is preferably digitized to produce a stream of digitized audio samples which may be stored as part of an event summary 530 in a memory 518. A user interface 514 may consist of the display 522, an audio speaker (not shown), and front panel buttons such as the on-off button 518 and shock button 524 for providing user control as well as visual and audible prompts. A clock 516 provides real-time clock data to the controller 506 for time-stamping information contained in the event summary 530. The memory 518, implemented either as on-board RAM, a removable memory card, or a combination of different memory technologies, operates to store the event summary 530 digitally as it is compiled during the treatment of the patient. The event summary 530 may include the streams of digitized ECG, audio samples, and other event data, as previously described. The event summary generally can be ported to another analysis or workstation or defibrillator either by wire or wireless transmission or by removing portable digital media which stores the event summary for transfer to another device.

In accordance with the principles of the present invention the ECG front end 502 is also configured to transmit a low level signal, under control of the controller 506, to measure patient impedance. As is known, patient impedance can be measured during shock delivery by monitoring the voltage and/or current of the shock pulse. At other times the patient impedance can be measured by injecting a low level signal into the patient from one electrode 416, receiving the response thereto on the other electrode, and measuring the detected response to determine patient impedance. In the example of a protocol of the present invention described below, the low signal injection technique is employed for the purpose of detecting CPR chest compressions. The force of a chest compression sharply changes the physiological path traveled by the signal, causing a detectable change in the received signal. Hence, small signals can be injected continuously with periodic significant changes in the response being identified as due to chest compressions. The low level response signals received by the ECG front end 502 are processed by the controller 506 with the changes being noted as chest compressions which affect the ECG and make the ECG signal unreliable for arrhythmia analysis at that time.

Another technique for detecting the occurrence of chest compressions disruptive to the ECG signal is to use the signals produced by a "smart" CPR puck. A CPR puck is a pad-like device which is placed on the chest of the patient and against which the chest compressions are applied. A "smart" CPR puck contains a sensor such as a force transducer or accelerometer which produces a signal each time the CPR puck receives the force of a chest compression. See U.S. Pat. No. 6,306,107 (Myklebust et al.) which describes a device which uses a pressure pad as a CPR puck containing an accelerometer and a force activated switch to determine the depth of depressions. One or more of these signals can be used in an implementation of the present invention to detect the occurrence of CPR chest compressions.

Figure 4:
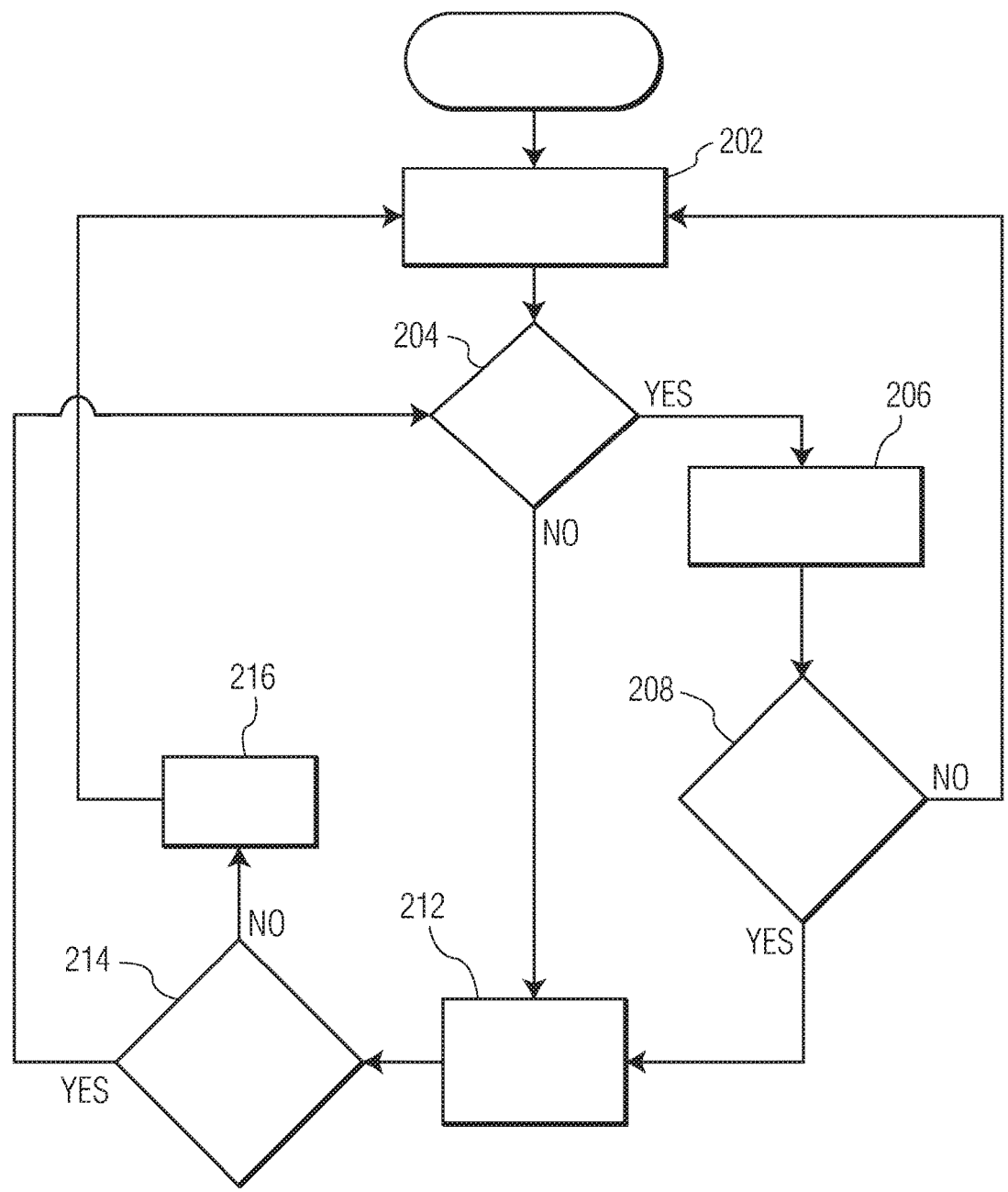
FIG. 4 is a flow diagram of a defibrillator operating protocol incorporating a CPR pause mode of operation.

An AED with a mode of operation including a "CPR pause" period is illustrated in FIG. 4. Since studies have shown that early CPR can play a critical role in patient recovery, this mode is becoming increasingly popular as an AED resuscitation protocol. Following attachment of the electrodes to the patient, the AED analyzes the patient's cardiac rhythm at step 202. During the analysis, the AED is precharged in preparation for delivery of electrotherapy. Based on the analysis, a determination is made at step 204 whether to advise the delivery of electrotherapy. If the analysis reveals a "shockable rhythm" in the patient's cardiac rhythm, delivery of electrotherapy is advised and at step 206 the AED is fully charged and a defibrillation pulse is delivered to resuscitate the patient in response to the user pressing the shock button on the AED. This sequence can be repeated two additional times if the patient has not been resuscitated and a shockable rhythm is detected, resulting in a total delivery of three shocks. Another protocol is a "single shock" protocol as described in U.S. patent application No. 60/751,268 (Snyder) filed Dec. 16, 2005. At the end of the shock sequence 208 or when a shock is not advised at 204, the AED enters a CPR pause period at 212. As CPR is performed by the rescuer, audio and/or visual prompts are used to instruct the rescuer on the proper administration of CPR. A synchronous tone may be produced by the AED to guide the rescuer in the proper rate of chest compressions. Typically, the CPR pause period is on the order of one minute or more. Toward the end of the CPR pause period the AED is precharged in preparation for a possible post-CPR shock delivery. At the conclusion of the CPR pause period the ECG is again analyzed for a shockable rhythm at 214 and if none is detected, the precharge is disarmed at 216 and the process returns to the initial rhythm analysis step 202. If a shockable rhythm is detected in this step, the protocol continues to advise a shock at 204 and deliver the shock at 206.

Figure 5:
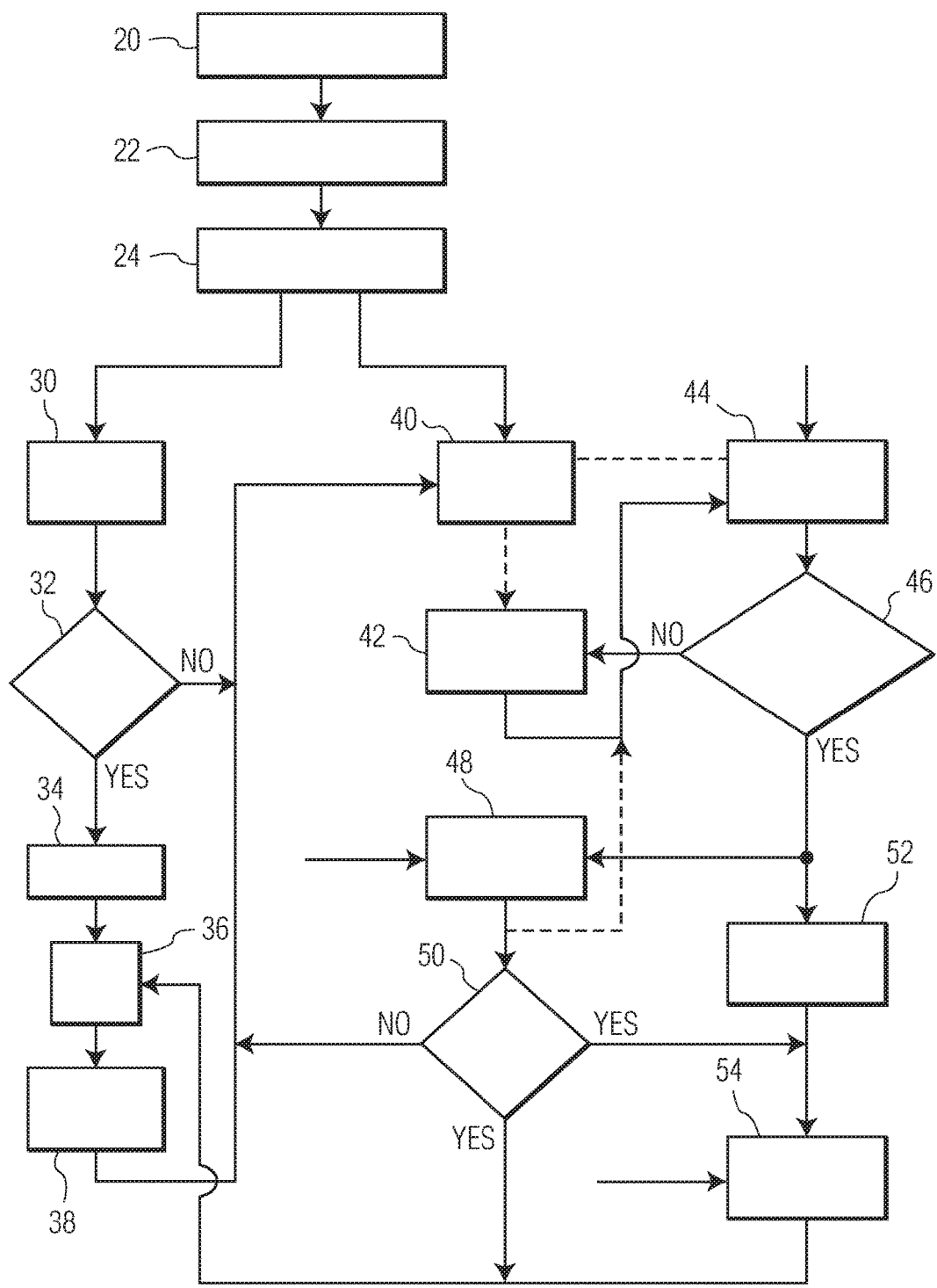
FIG. 5 is a flow diagram of a defibrillator operating protocol incorporating an interruptible CPR mode of operation in accordance with the principles of the present invention.

FIG. 5 illustrates a defibrillator operating protocol which includes an interruptible CPR period in accordance with the principles of the present invention. At step 20 the AED acquires the patient's ECG signal and analyzes the ECG data to produce a likelihood of return of spontaneous circulation (ROSC) score. The ROSC score is compared to a threshold to advise a treatment protocol which is more likely to be successful. See PCT application number IB2006/051897 (Snyder et al.), filed Jun. 13, 2006 which describes this technique, known commercially as "V-rhythm", as used in Philips Medical Systems defibrillators. The treatment protocol can be to shock the patient first, then perform CPR. Another possible treatment protocol is to provide CPR to the patient before delivering a shock. In the example of FIG. 5 the step 24 selects either a "shock first" protocol or a "CPR first" protocol.

The "shock first" protocol begins by performing ECG analysis at step 30. If a shock is advised at 32 as a result of the analysis, the AED charges for a shock at 34, arms the AED for shock delivery at 36, and prompts the rescuer to deliver the shock at 38. Following shock delivery the AED goes into a CPR period at 40.

In the "CPR first" protocol the AED begins by first prompting the rescuer to perform CPR on the patient at 40. In parallel the controller 506 monitors the patient impedance signal or "smart" CPR puck signal and looks for intervals during which an artifact-free ECG signal can be received. An ECG acquisition interval as short as four seconds can be sufficient to enable a quick analysis of the ECG data to determine if a shockable rhythm is present. However, CPR is generally delivered at a rate of about one hundred compressions per minute and CPR administration at this rate will thwart attempt to acquire a clean ECG signal for four seconds. But if the rescuer is interrupted or pauses to rest for a few seconds or interrupts chest compressions to ventilate the patient, e.g., by mouth-to-mouth resuscitation, this interval will be evidenced by a continuously stable patient impedance and/or lack of compression signals from the CPR puck, and an ECG signal of sufficient duration may be captured for a quick ECG analysis at 44.

However, if the administration of CPR is rapid and continuous, there will be no occurrence of a successful quick ECG analysis at 46 and, after a predetermined period of CPR administration such as a full minute, the rescuer is prompted to pause in the administration of CPR compressions at 42. With the CPR compressions interrupted at 42, as evidenced by the patient impedance or "smart" puck signal, a clean ECG signal can be acquired for the necessary duration and analyzed at 44. When the necessary ECG signal has been acquired or the quick ECG analysis is successful at 46, the rescuer is prompted at 48 to complete the administration of CPR and the AED is in its CPR pause mode until the CPR period is complete. Alternatively, if the analysis of the ECG data indicates that a shock is advised, the protocol can terminate any further CPR and proceed immediately to shock delivery 34, 36, 38. Toward the end of the CPR period in the protocol of FIG. 5, the HV delivery circuit 308 can be precharged as described in the aforementioned U.S. Pat. No. 6,553,257 (Snyder et al.) and US patent application publication no. 2006/0116724 (Snyder).

At the conclusion of the CPR period, based on the result of the quick ECG analysis, a shockable rhythm may have been identified and a shock is then advised at 50. The AED is armed at 36 and the shock delivered at 38. A variation of this is indicated by the dashed line between step 48 and step 44, which is to perform another ECG acquisition and quick ECG analysis at the end of the CPR period to verify that a shockable rhythm is still present before advising a shock sequence. But if a shock is not advised, the AED will return to the CPR pause mode for the administration of more CPR. Alternatively, in other protocols, the AED may enter a monitoring mode in which further monitoring and analysis of the ECG data is performed.

It may be seen from the foregoing that the identification of a shockable rhythm can be determined with only a short interruption to CPR. Since chest compressions are not applied during the interruption, the ECG data acquired is not contaminated by compression artifacts and is reliable for arrhythmia analysis. As a result, an advice to shock can be given immediately after the patient has received the benefit of a full period of CPR.

Variations to the protocol of FIG. 5 will readily occur to those skilled in the art. One variation of the protocol is to perform a V-rhythm analysis 52 of the ECG data used for the quick ECG analysis to determine whether a successful resuscitation is indicated. If the quick ECG analysis indicates that a shock is advised and the V-rhythm analysis indicates that electrotherapy is likely to be successful, the CPR period is interrupted at 54. While the rescuer is being prompted to cease CPR the HV delivery circuitry is precharged so that the AED can be quickly armed and a shock delivered. In instances where a high likelihood of a successful resuscitation is determined, this variation is likely to provide treatment best suited to the patient.

What is claimed is:

1. A method for using a defibrillator to provide resuscitation therapy to a patient, comprising:
    obtaining an electrocardiogram (ECG) signal via defibrillation electrodes;
    prompting a rescuer with the defibrillator to commence a cardio-pulmonary resuscitation (CPR) period in which the defibrillator prompts to perform CPR;
    monitoring the CPR period for the occurrence of an interval of a predetermined duration during which an ECG signal uncontaminated by compression artifact may be acquired;
    if the predetermined duration occurs,
    acquiring ECG data from the ECG signal that was obtained during the interval;
        if the predetermined duration does not occur, issuing a visual or audible prompt for interrupting the CPR period, and acquiring ECG data from the ECG signal that is obtained during the interruption; and
    resuming the CPR period.

2. The method of claim 1 further comprising:
    analyzing the acquired ECG data for a shockable rhythm.

3. The method of claim 2, further comprising:
    terminating further CPR and delivering electrotherapy from a high-voltage energy source if a shockable rhythm is indicated.

4. The method of claim 2, further comprising delivering electrotherapy at the conclusion of the resumed CPR period if the analyzing step indicates a shockable rhythm.

5. The method of claim 1, wherein the monitoring step further comprises:
    monitoring for CPR compressions during the CPR period.

6. The method of claim 5, wherein monitoring for CPR compressions further comprises:
    monitoring a patient impedance.

7. The method of claim 6, wherein monitoring the patient impedance further comprises applying a low level signal by means of an electrode and monitoring a response thereto.

8. The method of claim 7, wherein monitoring for CPR compressions further comprises:
    monitoring a signal produced in response to a sensed force of a chest compression.

9. A method for using a defibrillator to provide resuscitation therapy to a patient, comprising:
    obtaining an electrocardiogram (ECG) signal via defibrillation electrodes;
    prompting a rescuer with the defibrillator to commence a CPR period during which CPR chest compressions may be applied to the patient;

monitoring during the CPR period for an interval when ECG signals can be acquired without contamination by chest compression artifacts;

prior to the end of the CPR period, if no such interval has occurred, prompting the rescuer to interrupt the CPR chest compressions; and acquiring ECG signals which are not contaminated by chest compression artifacts during either of the interval and the prompted interruption.

10. The method of claim 9, further comprising:
performing an analysis of acquired ECG signals for a shockable rhythm.

11. The method of claim 10, further comprising:
prior to the termination of the resumed CPR period, precharging the defibrillator; and
following the termination of the CPR period, delivering a defibrillation shock sequence to the patient if the analysis of acquired ECG signal has indicated a shockable rhythm.

12. The method of claim 10, further comprising:
if the analysis of acquired ECG signals has indicated a shockable rhythm, analyzing the ECG signal data to estimate the likelihood of a successful resuscitation; and
if a successful resuscitation is likely, terminating any ongoing CPR for the delivery of a defibrillation shock sequence to the patient.

13. The method of claim 9, wherein monitoring during the CPR period further comprises monitoring for chest compressions by one of monitoring patient impedance or monitoring for signals produced in response to a force of a chest compression.

* * * * *